(12) United States Patent
Rajagopalan et al.

(10) Patent No.: US 10,329,215 B2
(45) Date of Patent: Jun. 25, 2019

(54) PROCESS FOR CONVERTING A NATURAL GAS FEEDSTOCK WITH INERT CONTENT TO CHEMICAL INTERMEDIATES

(71) Applicant: Sabic Global Technologies, B.V., Bergen Op Zoom (NL)

(72) Inventors: Vijayanand Rajagopalan, Bangalore (IN); Robert Broekhuis, Richmond, TX (US); Pankaj Singh Gautam, Sugar Land, TX (US); Vidya Sagar Reddy Sarsani, Pearland, TX (US)

(73) Assignee: Sabic Global Technologies, B.V., Bergen Op Zoom (NL)

( * ) Notice: Subject to any disclaimer, the term of this patent is extended or adjusted under 35 U.S.C. 154(b) by 0 days.

(21) Appl. No.: 16/249,405

(22) Filed: Jan. 16, 2019

(65) Prior Publication Data
US 2019/0144359 A1 May 16, 2019

Related U.S. Application Data

(63) Continuation of application No. PCT/US2018/032128, filed on May 10, 2018.
(Continued)

(51) Int. Cl.
*C07C 2/84* (2006.01)
(52) U.S. Cl.
CPC ..................... *C07C 2/84* (2013.01)
(58) Field of Classification Search
CPC .. C07C 11/04; C07C 2/84; C07C 9/04; C07C 5/327; C07C 1/12; C07C 9/06;
(Continued)

(56) References Cited

U.S. PATENT DOCUMENTS

| 4,461,630 A | 7/1984 | Cassidy et al. |
| 4,876,409 A | 10/1989 | Leyshon et al. |

(Continued)

FOREIGN PATENT DOCUMENTS

| AU | 2013355038 A1 | 6/2014 |
| CN | 205850523 U | 1/2017 |

(Continued)

OTHER PUBLICATIONS

Foreign communication from the priority application—International Application No. PCT/US2018/032128, International Search Report and Written Opinion of the International Searching Authority, dated Sep. 28, 2018, 9 pages.

(Continued)

*Primary Examiner* — Sharon Pregler
(74) *Attorney, Agent, or Firm* — Conley Rose, P.C.; Rodney B. Carroll

(57) ABSTRACT

A methane conversion process for producing $C_{2+}$ hydrocarbons comprising (a) introducing a reactant mixture comprising methane (>20 mol %) and an inert compound to a reaction unit to produce a reactor effluent stream comprising $C_{2+}$ hydrocarbons, methane, the inert compound, and water and/or carbon dioxide; (b) removing at least a portion of the water and/or at least a portion of the carbon dioxide from the reactor effluent stream to produce a demethanizer feed stream; (c) feeding at least a portion of the demethanizer feed stream to a demethanizer unit to produce two or more vapor streams (methane rich stream and inert rich stream), and at least one liquid stream ($C_{2+}$ hydrocarbons); (d) withdrawing at least a portion of the inert rich stream as a purge stream; (e) recycling any remaining portion of the inert rich stream to the reaction unit; and (f) recycling the methane rich stream to the reaction unit.

20 Claims, 1 Drawing Sheet

Related U.S. Application Data

(60) Provisional application No. 62/576,514, filed on Oct. 24, 2017.

(58) Field of Classification Search
CPC ........... C07C 2/82; C07C 1/0425; C07C 1/04; C07C 1/0485; C07C 29/1518; C07C 5/09; C07C 31/04; C07C 1/041; C07C 2523/10; C07C 2523/652; C07C 2/78; C07C 4/02; C07C 4/04; C07C 5/32; B01J 19/245; B01J 23/00; B01J 23/10; B01J 23/20; C10G 2400/02; C10G 50/00; C10G 2300/1025; C10G 2400/04; C10G 27/04; C10G 29/205; C10G 31/06; C10G 69/126
See application file for complete search history.

(56) References Cited

U.S. PATENT DOCUMENTS

| | | | |
|---|---|---|---|
| 8,815,080 | B2 | 8/2014 | Sundaram |
| 9,701,597 | B2* | 7/2017 | Rafique ................. C07C 2/84 |
| 2015/0152025 | A1 | 6/2015 | Cizeron et al. |
| 2015/0307415 | A1 | 10/2015 | Rafique et al. |
| 2015/0329439 | A1 | 11/2015 | Nyce et al. |
| 2016/0272556 | A1 | 9/2016 | Rafique et al. |
| 2016/0289143 | A1 | 10/2016 | Duggal et al. |
| 2017/0137355 | A1 | 5/2017 | Sarsani et al. |
| 2017/0219281 | A1 | 8/2017 | Andre et al. |

FOREIGN PATENT DOCUMENTS

| | | |
|---|---|---|
| EP | 0489555 A1 | 6/1992 |
| JP | 2010524684 A | 7/2010 |
| KR | 20110082580 A | 7/2011 |
| WO | 2004103936 A1 | 12/2004 |
| WO | 201789937 A2 | 6/2017 |

OTHER PUBLICATIONS

Grande, Carlos A., "Advances in Pressure Swing Adsorption for Gas Separation," ISRN Chemical Engineering, 2012, 13 pages, vol. 2012.

Lunsford, Jack H., "Catalytic conversion of methane to more useful chemicals and fuels: a challenge for the 21st century," Catalysis Today, 2000, pp. 165-174, vol, 63, Elsevier Science B.V.

Mleczko, L., et al., "Catalytic oxidative coupling of methane—reaction engineering aspects and process schemes," Fuel Processing Technology, 1995, pp. 217-248, vol. 42, Elsevier Science B.V.

Wang, Dingjun, et al., "Oxidative Coupling of Methane over Oxide-Supported Sodium-Manganese Catalysts," Journal of Catalysis, 1995, pp. 390-402, vol. 155, Academic Press Inc.

Wang, Ye, et al., "Catalytic Oxidation of Methane to Methanol initiated in a Gas Mixture of Hydrogen and Oxygen," Journal of the Chemical Society, Chemical Communications, 1994, pp. 2209-2210, vol. 19.

Wozny, Gunter, et al., "Oxidative Coupling of Methane: A Design of Integrated Catalytic processes," Chemical Engineering Transactions, 2010, pp. 1399-1404, vol. 21.

Filing Receipt and Specification of U.S. Appl. No. 62/576,514, filed Oct. 24, 2017, 54 pages.

Filing Receipt and Specification of PCT Application No. PCT/US20181032128 filed May 10, 2018, 34 pages.

* cited by examiner

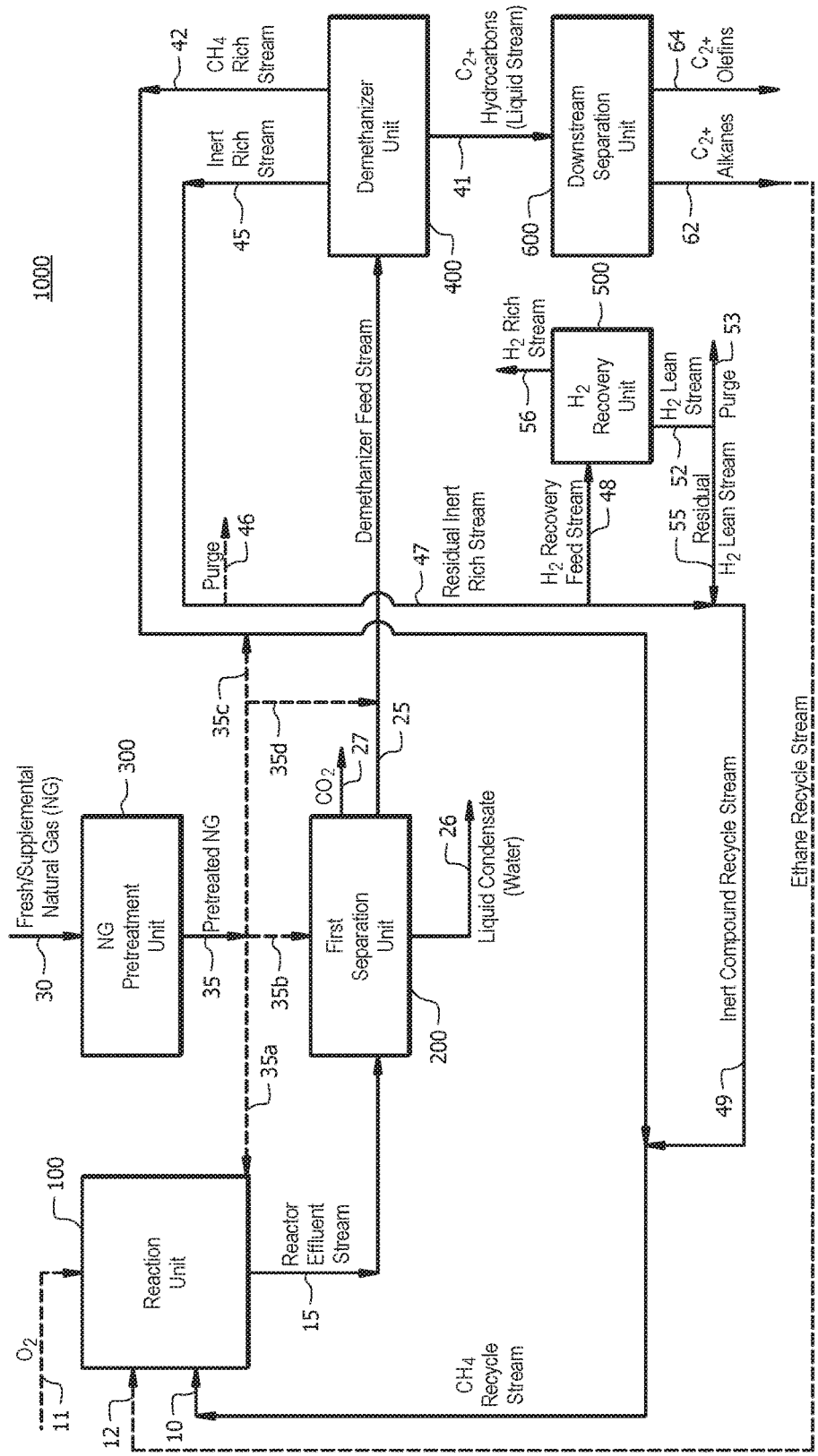

PROCESS FOR CONVERTING A NATURAL GAS FEEDSTOCK WITH INERT CONTENT TO CHEMICAL INTERMEDIATES

CROSS-REFERENCE TO RELATED APPLICATIONS

This application is a continuation of and claims priority to International Application No. PCT/US2018/032128 filed May 10, 2018 and entitled "A Process for Converting a Natural Gas Feedstock with Inert Content to Chemical Intermediates," which claims priority to U.S. Provisional Application No. 62/576,514 field Oct. 24, 2017 and entitled "Process for Producing Light Olefins from Natural Gas Feedstock with Inert Content," each of which applications is incorporated by reference herein in its entirety.

TECHNICAL FIELD

The present disclosure relates to methods of producing hydrocarbons, more specifically methods of producing olefins by a methane partial conversion process, such as oxidative coupling of methane.

BACKGROUND

In methane partial conversion processes (e.g., oxidative coupling of methane (OCM) process, single-step methane to olefins conversion process, etc.), natural gas comprising primarily methane along with other hydrocarbons and inerts (such as nitrogen) is converted to chemical intermediates (e.g., olefins, such as ethylene and propylene; alkanes, such as ethane and propane). Depending on where the natural gas is sourced, the inerts (e.g., nitrogen) content in the natural gas can be relatively high (2-7 mol %). Such inerts content poses a challenge in terms of processing in a recycle process, as inerts tend to build up in recycle streams. Further, such inerts content can lead to large recycle rates in the process, as well as potentially reduced reaction efficiency due to dilution of the reactants, thus leading to larger sizes of major equipment such as reactors, compressors and columns.

A conventional method of dealing with the issue of high inerts content is to increase the purge rate from the process so as to reduce the concentration of inerts (e.g., nitrogen) in recycle loops. However, unconverted methane is also lost from the process in this purge, which means that this approach requires an increased make-up feed rate and results in a lower carbon efficiency of the overall conversion process. While the purge gas can be burned to generate power, this approach would require investment in the form of power plant equipment. Thus, there is an ongoing need for the development of methane partial conversion processes that minimize inerts content in recycle loops via process modifications which do not result in large capital investments in the compression and separation equipment.

DESCRIPTION OF THE DRAWINGS

For a detailed description of the preferred aspects of the disclosed methods, reference will now be made to the accompanying drawing in which:

The FIGURE displays a schematic of a system for a methane partial conversion process.

DETAILED DESCRIPTION

Disclosed herein are methane partial conversion processes (e.g., for the production of light alkanes or olefins, such as ethylene, ethane, propylene, and propane), wherein methane can be sourced as natural gas which has a relatively high inert gas content (e.g., greater than 0.1 mol %, such as 2-7 mol %, wherein the inert gas can be predominantly nitrogen), wherein a purge rate from such processes is reduced by withdrawing the purge from an overhead stream in a demethanizer section of a separation sequence, and wherein such overhead stream is enriched in inert components. In some aspects, a hydrogen recovery unit (e.g., employing methods such as pressure swing adsorption or membrane separation) can be positioned in the overhead stream enriched in inert components, with the purge flow withdrawn downstream of the recovery unit from a process stream that is even further enriched in the inert gas.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and the ranges are inclusive of the recited endpoints. Unless expressly indicated otherwise, the various numerical ranges specified in this application are approximations. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Referring to the configuration of the FIGURE, a $C_{2+}$ hydrocarbons production system 1000 is disclosed. The $C_{2+}$ hydrocarbons production system 1000 generally comprises a reaction unit (e.g., an oxidative coupling of methane (OCM) reaction unit) 100; a first separation unit 200; a natural gas (NG) pretreatment unit 300; a demethanizer unit 400; a hydrogen ($H_2$) recovery unit 500; and a downstream separation unit (e.g., second separation unit) 600. As will be appreciated by one of skill in the art, and with the help of this disclosure, $C_{2+}$ hydrocarbons production system components can be in fluid communication with each other through any suitable conduits (e.g., pipes, streams, etc.). While the current disclosure will be discussed in detail in the context of a methane partial conversion process for the production of $C_{2+}$ hydrocarbons (e.g., an OCM process for the production of light olefins), it should be understood that the methods disclosed herein can be used in conjunction with any suitable process that recycles a stream with inerts (i.e., inert compounds) content compatible with the methods and materials disclosed herein.

In an aspect, a methane conversion process for producing $C_{2+}$ hydrocarbons as disclosed herein can comprise a step of introducing a reactant mixture to the reaction unit 100 to produce a reactor effluent stream 15; wherein the reactant mixture comprises a hydrocarbon, e.g., methane ($CH_4$), and an inert compound; wherein the reactor effluent stream 15 comprises $C_{2+}$ hydrocarbons, methane, the inert compound, and water and/or carbon dioxide; and wherein the mole fraction of methane in the reactant mixture is greater than the mole fraction of methane in the reactor effluent stream 15. The reaction unit 100 comprises a methane conversion unit. As will be appreciated by one of skill in the art, and with the help of this disclosure, methane undergoes partial conversion in the reaction unit 100, and the partial conversion of methane results in the reactor effluent comprising unreacted methane, which leads to the need to separate such unreacted methane from the reactor effluent and recycle it to the reaction unit 100. In an aspect, a methane recycle stream 10 can be introduced to the reaction unit 100, wherein the methane recycle stream 10 is recovered from the reactor effluent stream 15, as will be disclosed in more detail later herein. The methane recycle stream 10 can provide the $CH_4$ for the reactant mixture. In some aspects, the methane recycle stream 10 can further comprise $H_2$, as will be disclosed in more detail later herein.

The reaction unit 100 can comprise any suitable methane conversion unit. For example, the reaction unit 100 can comprise an OCM reaction zone, a reaction zone for a single-step methane to olefins conversion, an optional methanation reaction zone, an optional thermal cracking reaction zone, an optional ethane pyrolysis reaction zone, and the like, or combinations thereof.

In an aspect, the reactant mixture can comprise a hydrocarbon or mixtures of hydrocarbons. In some aspects, the hydrocarbon or mixtures of hydrocarbons can comprise methane, natural gas, natural gas liquids, wet natural gas, and the like, or combinations thereof. In an aspect, methane can be present in the reactant mixture in a concentration of equal to or greater than about 20 mol %, greater than about 30 mol %, greater than about 40 mol %, or greater than about 50 mol %.

Referring to the configuration of the FIGURE, when the process is run for the first time (e.g., during start-up of $C_{2+}$ hydrocarbons production system 1000), a pretreated natural gas stream 35 can be introduced directly to the reaction unit 100, for example via stream 35a. Once a reactor effluent stream 15 is produced, and a methane recycle stream 10 is recovered from the reactor effluent stream 15, supplemental methane (e.g., additional methane; methane used in addition to the recycled methane) can be introduced to the $C_{2+}$ hydrocarbons production system 1000 at any suitable point or location, to provide for the necessary amount of methane in reaction unit 100. For example, a pretreated natural gas stream 35a can continue to be introduced directly to the reaction unit 100. Additionally or alternatively, a pretreated natural gas stream 35c comprising supplemental methane can be introduced to the reaction unit 100 via the methane recycle stream (e.g., via a methane rich stream 42). Additionally or alternatively, a pretreated natural gas stream 35b comprising supplemental methane can be run through additional purification steps, as will be disclosed in more detail later herein, and then through the demethanizer unit 400 to the methane recycle stream. Additionally or alternatively, a pretreated natural gas stream 35d comprising supplemental methane can be introduced to the demethanizer unit 400, for example via a demethanizer feed stream 25.

In an aspect, the reactant mixture can further comprise oxygen ($O_2$). For example, in an OCM process, the reactant mixture can comprise $CH_4$ and $O_2$. In an OCM process, $CH_4$ is oxidatively converted into ethane ($C_2H_6$), and ethylene ($C_2H_4$).

In an aspect, an $O_2$-containing stream 11 can be provided to the reaction unit 100 (e.g., OCM reaction unit). Stream 11 can be oxygen gas, technical oxygen (which can contain some air), air, oxygen enriched air, and the like, or combinations thereof. In an OCM process, the reactant mixture can be characterized by a $CH_4/O_2$ molar ratio of from about 2:1 to about 40:1, or from about 5:1 to about 10:1.

In an aspect, the reactant mixture can comprise one or more inert compounds. The inert compounds do not participate to a significant extent in the methane conversion reaction that takes place in the reaction unit 100. In an aspect, the inert compounds can comprise nitrogen and/or argon. The inert compounds can be introduced to the reaction unit 100 along with the methane, for example as a natural gas component (e.g., nitrogen), as an oxidant gas component (e.g., nitrogen and/or argon), etc.

In an aspect, a methane conversion process for producing $C_{2+}$ hydrocarbons as disclosed herein can comprise conducting a methane conversion process in the presence of any suitable methane conversion catalyst. For example, an OCM reaction can be conducted in the presence of an OCM catalyst. In some aspects, the OCM catalyst can comprise basic oxides; mixtures of basic oxides; redox elements; redox elements with basic properties; mixtures of redox elements with basic properties; mixtures of redox elements with basic properties promoted with alkali and/or alkaline earth metals; rare earth metal oxides; mixtures of rare earth metal oxides; mixtures of rare earth metal oxides promoted by alkali and/or alkaline earth metals; and the like; or combinations thereof.

In some aspects, the reactant mixture can be introduced to the reaction unit 100 at a temperature of from about 0° C. to about 500° C., or from about 25° C. to about 300° C. As will be appreciated by one of skill in the art, and with the help of this disclosure, the temperature at which the reactant mixture is introduced to the reaction unit 100 can be selected such that, when the exothermic heat of oxidation in the reaction unit is taken into consideration, the conditions within the reaction unit are effective to promote the desired partial oxidation reaction.

In an aspect where the methane conversion process comprises an OCM process, an OCM reaction zone can be characterized by a temperature of from about 700° C. to about 1,100° C., or from about 750° C. to about 1,000° C.

In some aspects, the reaction unit 100 can further comprise an ethane pyrolysis reaction zone. Ethane can be subjected to pyrolysis or thermal cracking in the ethane pyrolysis reaction zone to form $C_2H_4$ and $H_2$. Generally, a cracking reaction refers to a reaction by which a saturated hydrocarbon or mixture of saturated hydrocarbons is broken down into smaller molecules and/or unsaturated molecules. In the case of ethane cracking, $C_2H_6$ is converted to $C_2H_4$ and $H_2$. As will be appreciated by one of skill in the art, and with the help of this disclosure, the partial conversion of methane can result in the reactor effluent comprising ethane, and provided that ethane conversion during ethane pyrolysis is not 100%, ethane can be separated from the reactor effluent and recycled to the reaction unit 100 (e.g., to the ethane pyrolysis reaction zone). In an aspect, an ethane recycle stream 12 can be introduced to the reaction unit 100, wherein the ethane recycle stream 12 is recovered from the reactor effluent stream 15, as will be disclosed in more detail later herein. The ethane recycle stream 12 can provide at least a portion of the $C_2H_6$ for the ethane pyrolysis reaction zone. In some aspects, the ethane recycle stream 12 can be supplemented with ethane from an external source prior to introducing the ethane recycle stream 12 to the reaction unit 100 (e.g., to the ethane pyrolysis reaction zone).

In an aspect, the ethane pyrolysis reaction zone can be characterized by a temperature of from about 750° C. to about 1,000° C., from about 775° C. to about 975° C., or from about 800° C. to about 950° C.

The reactor effluent stream 15 can comprise $C_{2+}$ hydrocarbons, methane, the inert compounds, and water and/or carbon dioxide; wherein the mole fraction of methane in the reactant mixture is greater than the mole fraction of methane in the reactor effluent stream 15. In some aspects, the reactor effluent stream 15 can further comprise $H_2$ and/or carbon monoxide (CO). The $C_{2+}$ hydrocarbons can comprise $C_{2+}$ olefins and $C_{2+}$ alkanes. The $C_{2+}$ hydrocarbons can comprise $C_2$ hydrocarbons and $C_{3+}$ hydrocarbons, wherein the $C_{2+}$ hydrocarbons can comprise ethylene ($C_2H_4$) and ethane ($C_2H_6$). The $C_{2+}$ hydrocarbons can further comprise acetylene ($C_2H_2$). The $C_{3+}$ hydrocarbons can comprise $C_3$ hydrocarbons, $C_4$ hydrocarbons ($C_4s$), and $C_{5+}$ hydrocarbons; wherein the $C_3$ hydrocarbons can comprise propylene ($C_3H_6$) and propane ($C_3H_8$).

In an aspect, a methane conversion process for producing $C_{2+}$ hydrocarbons as disclosed herein can comprise a step of removing at least a portion of the water (e.g., recovered via liquid condensate stream 26) and/or at least a portion of the carbon dioxide ($CO_2$) (e.g., recovered via $CO_2$ stream 27) from the reactor effluent stream 15 in the first separation unit 200 to produce a demethanizer feed stream 25. The first separation unit 200 can comprise one or more compressors, one or more heat exchangers, a water quench vessel, a $CO_2$ separator, and the like.

In some aspects, the reactor effluent stream 15 can comprise water. In other aspects, the reactor effluent stream 15 can comprise $CO_2$. In yet other aspects, the reactor effluent stream 15 can comprise both water and $CO_2$. As will be appreciated by one of skill in the art, and with the help of this disclosure, in aspects where the reactor effluent stream 15 comprises both water and $CO_2$, the water has to be removed prior to $CO_2$ removal.

In aspects where the reactor effluent stream 15 comprises water, at least a portion of the water can be removed from the reactor effluent stream 15 to yield a dehydrated reactor effluent stream. As will be appreciated by one of skill in the art, and with the help of this disclosure, any suitable combination of cooling and compressing the reactor effluent stream 15 can be used to promote water condensation, removal, and recovery via liquid condensate stream 26.

As will be appreciated by one of skill in the art, and with the help of this disclosure, when the reactor effluent stream 15 comprises water but does not comprise $CO_2$, the demethanizer feed stream 25 and the dehydrated reactor effluent stream are the same stream (i.e., the dehydrated reactor effluent stream is the demethanizer feed stream 25). Further, and as will be appreciated by one of skill in the art, and with the help of this disclosure, when the reactor effluent stream 15 comprises both water and $CO_2$, the dehydrated reactor effluent stream can be subjected to a step of $CO_2$ removal to produce the demethanizer feed stream 25, as will be disclosed in more detail later herein. Furthermore, and as will be appreciated by one of skill in the art, and with the help of this disclosure, when the reactor effluent stream 15 comprises $CO_2$ but does not comprise water, the reactor effluent stream 15 can be subjected to a step of $CO_2$ removal to produce the demethanizer feed stream 25, as will be disclosed in more detail later herein.

In some aspects, removing at least a portion of the water from the reactor effluent stream 15 can comprise cooling at least a portion of the reactor effluent stream 15, for example in a heat exchanger, to reduce the temperature of the reactor effluent stream 15, thereby promoting water condensation. A cooled reactor effluent stream can be further compressed to promote water condensation and recovery via liquid condensate stream 26.

In an aspect, a cooled reactor effluent stream can be introduced to a water quench vessel or tower to yield the dehydrated reactor effluent stream and a liquid condensate stream 26 comprising water.

In an aspect, at least a portion of the $CO_2$ can be removed from the dehydrated reactor effluent stream and/or the reactor effluent stream 15 to yield the demethanizer feed stream 25. The demethanizer feed stream 25 can comprise $C_{2+}$ hydrocarbons, methane, and the inert compound. In some aspects, the demethanizer feed stream 25 can comprise $H_2$ and/or CO.

In some aspects, at least a portion the dehydrated reactor effluent stream and/or the reactor effluent stream 15 can be introduced to a $CO_2$ separator (e.g., $CO_2$ scrubber) to yield the demethanizer feed stream 25 and a $CO_2$ stream 27. Optionally, the dehydrated reactor effluent stream can be compressed prior to introducing to the $CO_2$ separator.

The $CO_2$ separator can comprise $CO_2$ removal by amine (e.g., monoethanolamine) absorption (e.g., amine scrubbing), pressure swing adsorption, temperature swing adsorption, gas separation membranes (e.g., porous inorganic membranes, palladium membranes, polymeric membranes, zeolites, etc.), cryogenic separation, and the like, or combinations thereof. In an aspect, the $CO_2$ separator can comprise $CO_2$ removal by amine absorption.

In an aspect, the demethanizer feed stream 25 can comprise $CO_2$ in a negligible amount, such as less than about 1 mol %, less than about 0.1 mol %, or less than about 0.01 mol %.

In an aspect, the dehydrated reactor effluent stream and/or the demethanizer feed stream 25 can comprise water in a negligible amount, such as less than about 1 mol %, less than about 0.1 mol %, or less than about 0.01 mol %

In some aspects, the dehydrated reactor effluent stream and/or the reactor effluent stream 15 can be combined with at least a portion of the pretreated natural gas stream 35*b* prior to entering the $CO_2$ separator.

In an aspect, a natural gas stream 30 (e.g., supplemental natural gas, fresh (as opposed to recycled) natural gas) can be introduced to the natural gas pretreatment unit 300. In an aspect, the natural gas stream 30 can comprise natural gas. Generally, natural gas comprises mostly methane, but can also contain light alkanes such as ethane and propane, as well as heavier hydrocarbons; in addition to small amounts of nitrogen, carbon dioxide, sulfur-containing compounds (e.g., $H_2S$), and water. In some aspects, the natural gas stream 30 can further comprise a methane stream from a refinery and/or processing plant. For example, light alkanes, including methane, can often be separated in a refinery during processing of crude oil into various products, and a methane stream can be provided from the same refinery, a different refinery, and/or a refinery off gas. The methane stream can include a stream from combinations of different sources (e.g., streams from different refineries, different streams from the same refinery, etc.). The methane stream can be provided from a remote location and initial processing of the stream (e.g., refining or partial refining) can occur at the remote location to remove certain contaminants; the refining or partial refining can occur on site where the $C_{2+}$ hydrocarbons production process is conducted; or both.

In some aspects, the natural gas pretreatment unit 300 can comprise a desulphurization unit, sometimes referred to as a scrubbing or sweetening unit. The natural gas stream 30 can comprise sulfur-containing compounds (e.g., $H_2S$, $SO_x$, such as $SO_2$, S, and/or $RS_yR'$ type compounds). In an aspect, at least a portion of the sulfur-containing compounds can be removed from the natural gas stream 30 in the natural gas pretreatment unit 300, for example by amine (e.g., monoethanolamine, diethanolamine, etc.) absorption, or by using a solid sorbent (e.g., zinc oxide or activated carbon). As will be appreciated by one of skill in the art, and with the help of this disclosure, when the dehydrated reactor effluent stream is combined with the pretreated natural gas stream 35b prior to entering the $CO_2$ separator, any residual sulfur-containing compounds entering the $CO_2$ separator would be removed along with the $CO_2$, when the $CO_2$ separation process is based on amine absorption. Further, and as will be appreciated by one of skill in the art, and with the help of this disclosure, when the dehydrated reactor effluent stream is combined with the pretreated natural gas stream 35b prior to entering the $CO_2$ separator, $CO_2$ introduced to the dehydrated reactor effluent stream via the supplemental methane would also be removed in the $CO_2$ separator.

The pretreated natural gas stream 35 (35a, 35b, 35c, 35d) can be produced by desulphurization of a natural gas stream 30. The natural gas stream 30 provides for supplemental methane (e.g., methane in addition to recycled methane) being introduced to the $C_{2+}$ hydrocarbons production system 1000, for example to account for methane converted in the reaction unit 100 and any methane lost during recovering and recycling the unreacted methane. The pretreated natural gas stream 35 can comprise methane and the inert compound. The inert compound can be present in the pretreated natural gas stream 35 in a mole fraction of equal to or greater than about 0.001, equal to or greater than about 0.005, equal to or greater than about 0.01, equal to or greater than about 0.02, from about 0.001 to about 0.2, from about 0.005 to about 0.15, from about 0.01 to about 0.1, or from about 0.02 to about 0.08. As will be appreciated by one of skill in the art, and with the help of this disclosure, the pretreated natural gas stream 35 can comprise any suitable amount of inert compound, such as an amount of inert compound that is conventionally encountered in natural gas.

The demethanizer unit serves to separate light components such as methane, hydrogen, carbon monoxide, and inert compounds from heavier components such as $C_{2+}$ hydrocarbons. The separation process comprises various suboperations such as compression, refrigeration, heat exchange, partial condensation, expansion, and/or fractionation. These operations are connected via process piping conveying intermediate vapor and liquid streams. Any (number) of these streams may combined and/or split to create additional intermediate streams, which may be directed toward one of the suboperations or recovered as a demethanizer product stream.

In an aspect, a methane conversion process for producing $C_{2+}$ hydrocarbons as disclosed herein can comprise a step of feeding at least a portion of the demethanizer feed stream 25 to the demethanizer unit 400 to produce two or more vapor streams, and at least one liquid stream 41; wherein the two or more vapor streams comprise a methane rich stream 42 and an inert rich stream 45; wherein the mole fraction of methane in the methane rich stream 42 is greater than the mole fraction of methane in the inert rich stream 45; wherein the mole fraction of inert compound in the inert rich stream 45 is greater than the mole fraction of inert compound in the methane rich stream 42; and wherein the at least one liquid stream 41 comprises $C_{2+}$ hydrocarbons. As will be appreciated by one of skill in the art, and with the help of this disclosure, the mole fraction of methane in the methane rich stream 42 is greater than the mole fraction of methane in the demethanizer feed stream 25. Further, as will be appreciated by one of skill in the art, and with the help of this disclosure, the mole fraction of inert compound in the inert rich stream 45 is greater than the mole fraction of inert compound in the demethanizer feed stream 25.

In some aspects, the demethanizer unit 400 can comprise one or more flash vessels and at least one fractionation column; wherein the inert rich stream 45 can be recovered as an overhead stream from the one or more flash vessels, and optionally as an overhead stream from a fractionation column when more than one fractionation column is employed in the demethanizer unit 400; wherein the methane rich stream 42 can be recovered as an overhead stream from a fractionation column; and wherein the at least one liquid stream 41 can be recovered as a bottoms stream from a fractionation column. In aspects where more than one fractionation column is employed in the demethanizer unit 400, and as will be disclosed in more detail later herein, the inert rich stream 45 can comprise one or more overhead streams from the one or more flash vessels, as well as one or more overhead streams from the fractionation columns other than the fractionation column that produces the overhead methane rich stream 42.

The one or more flash vessels can be any suitable separation vessel(s) that can remove liquid droplets entrained in a gas stream (e.g., a gas liquid separator, a vapor liquid separator, a flash drum, a knock-out drum, a knock-out pot, etc.). The one or more flash vessels can employ pressure reduction for separating an overhead gas stream (e.g., an inert rich stream) from a liquid bottoms stream. In some aspects, one or more liquid bottoms streams can be recovered from the one or more flash vessels; wherein the one or more liquid bottoms streams recovered from the one or more flash vessels can be fed to the fractionation column.

The demethanizer unit 400 can comprise any suitable number and configuration of columns, wherein the columns can be in series and/or parallel.

In some aspects, the two or more vapor streams recovered from the demethanizer unit 400 can comprise the methane rich stream 42 and a plurality of inert rich streams 45. As will be appreciated by one of skill in the art, and with the help of this disclosure, when more than one flash vessel is employed in the demethanizer unit 400, more than one inert rich stream can be recovered from the flash vessels of the demethanizer unit 400, and such overhead inert rich streams recovered from the flash vessels are part of the plurality of inert rich streams 45. Further, as will be appreciated by one of skill in the art, and with the help of this disclosure, when more than one fractionation column is employed in the demethanizer unit 400, more than one overhead stream can be recovered from the fractionation columns of the demethanizer unit 400. For purposes of the disclosure herein, the methane rich stream 42 refers to the overhead stream with the highest methane content recovered from the fractionation columns of the demethanizer unit 400. Further, for purposes of the disclosure herein, any overhead streams other than the methane rich stream 42 recovered from the fractionation columns of the demethanizer unit 400 will be referred to as inert rich streams, which overhead inert rich streams are part of the plurality of inert rich streams 45. Furthermore, for purposes of the disclosure herein, any overhead streams recovered from the demethanizer unit 400 other than the methane rich stream 42 will be referred to as "inert rich stream" 45 (e.g., an inert rich stream 45, one or more inert rich streams 45, two or more inert rich streams 45, a plurality of inert rich streams 45, etc.). Demethanizer units are described in more detail in U.S. Publication Nos. 20160272556 A1 and 20160289143 A1; each of which is incorporated by reference herein in its entirety.

The methane rich stream 42 can be recycled to the reaction unit 100, for example via the methane recycle stream 10.

In an aspect, the inert rich stream 45 can comprise the inert compound in an amount of equal to or greater than about 1 mol %, equal to or greater than about 5 mol %, or equal to or greater than about 10 mol %. In an aspect, the inert rich stream 45 can further comprise $H_2$. For example, the inert rich stream 45 can comprise $H_2$ in an amount of equal to or greater than about 1 mol %, equal to or greater than about 5 mol %, or equal to or greater than about 10 mol %.

In an aspect, a methane conversion process for producing $C_{2+}$ hydrocarbons as disclosed herein can comprise a step of withdrawing at least a portion of the inert rich stream 45 as a purge stream 46, to yield a residual inert rich stream 47. For purposes of the disclosure herein, a "purge" or "purge stream" withdrawn from the inert rich stream 45 is defined as any portion of the inert rich stream 45 not being returned to the reaction unit 100. The purge or purge stream (e.g., stream 46 and/or stream 53, discussed in more detail below) can be vented, flared, used as fuel, used as a reagent in a different process, etc.

In an aspect, the residual inert rich stream 47 (e.g., any remaining portion of the inert rich stream 45) can be recycled to the reaction unit 100, for example via the methane recycle stream 10. In some aspects, the methane rich stream 42 can be combined with the residual inert rich stream 47 (e.g., any remaining portion of the inert rich stream 45) to form the methane recycle stream 10, wherein the methane recycle stream 10 can be recycled to the reaction unit 100.

In some aspects, two or more inert rich streams of a plurality of inert rich streams 45 can be combined to form a combined inert rich stream. In such aspects, the methane conversion process for producing $C_{2+}$ hydrocarbons as disclosed herein can further comprise (i) withdrawing at least a portion of the combined inert rich stream as a purge stream; and (ii) recycling any remaining portion of the combined inert rich stream to the reaction unit 100, for example via the methane recycle stream 10.

In aspects where two or more inert rich streams of a plurality of inert rich streams 45 are combined to form a combined inert rich stream, the methane conversion process for producing $C_{2+}$ hydrocarbons as disclosed herein can further comprise (1) withdrawing at least a portion of at least one inert rich stream of the two or more inert rich streams as a purge stream prior to forming the combined inert rich stream; and (2) recycling the combined inert rich stream to the reaction unit 100, for example via the methane recycle stream 10. In aspects where the purge is withdrawn from some of the inert rich streams, but not all inert rich streams, any remaining portion of the inert rich streams (whether it had a purge withdrawn or not) can be recycled to the reaction unit 100, for example via the methane recycle stream 10. Any streams of the remaining portion of the inert rich streams can be combined in any suitable manner with each other and/or with the methane rich stream 42, and then can be recycled to the reaction unit 100, for example via the methane recycle stream 10.

In some aspects, the demethanizer unit 400 can employ cooling of the one or more flash vessels and/or the at least one fractionation column, to provide for better separation of components in each vessel and/or column. For example, the at least one fractionation column can be a cryogenic distillation column. As will be appreciated by one of skill in the art, and with the help of this disclosure, when cooling of the vessels and/or columns in the demethanizer unit 400 is employed, the overhead streams recovered from the demethanizer unit 400 can have a relatively low temperature.

In an aspect, the temperature of the methane rich stream 42 can be increased by indirect heat exchange with at least one process stream. As will be appreciated by one of skill in the art, and with the help of this disclosure, the demethanizer unit 400 requires refrigeration to attain the low temperatures required for its performance. The need for refrigeration in the demethanizer unit 400 can be reduced by suitable use of heat exchange between relatively warm and cold streams within the demethanizer unit 400. Further, as will be appreciated by one of skill in the art, and with the help of this disclosure, the overhead streams recovered from the demethanizer unit 400 (e.g., methane rich stream 42, inert rich streams 45) are examples of relatively cold streams that could be exchanged against relatively warmer process streams (e.g., demethanizer feed stream 25). For example, the temperature of the methane rich stream 42 can be increased by indirect heat exchange with the demethanizer feed stream 25, wherein the temperature of the demethanizer feed stream 25 is decreased.

In an aspect, the temperature of the inert rich stream 45 can be increased by indirect heat exchange with at least one process stream prior to withdrawing at least a portion of the inert rich stream 45 as a purge stream 46. In such aspect, the at least one process stream can comprise the demethanizer feed stream 25. As will be appreciated by one of skill in the art, and with the help of this disclosure, the inert rich stream 45, or any combination of inert rich streams 45, should be heat exchanged prior to withdrawing a purge, such that none of the cooling capacity of the inert rich stream would be lost to the purge stream.

In an aspect, the inert rich stream 45 and/or the methane rich stream 42 can indirectly exchange heat with at least one process stream in any suitable heat exchange system, such as a cold box. Generally, a cold box refers to an insulated enclosure configured for heat exchange at fairly low temperatures (e.g., less than 0° C., cryogenic temperatures, etc.) and comprising one or more heat exchangers and associated equipment, such as pumps, piping, etc. A cold box can comprise one or more heat exchangers. In some aspects, the demethanizer unit 400 comprises the cold box used for indirect heat exchanging the demethanizer feed stream 25 with the inert rich stream 45 and/or the methane rich stream 42.

In aspects where the reactor effluent stream 15 further comprises $H_2$, a methane conversion process for producing $C_{2+}$ hydrocarbons as disclosed herein can comprise a step of feeding at least a portion of the inert rich stream 45 and/or at least a portion of the residual inert rich stream 47 (e.g., hydrogen recovery feed stream 48) to the hydrogen recovery unit 500 to produce a hydrogen rich stream 56 and hydrogen lean stream 52, wherein the mole fraction of hydrogen in the hydrogen rich stream 56 is greater than the mole fraction of hydrogen in the hydrogen lean stream 52. The hydrogen recovery unit 500 can be selected from a pressure swing adsorption (PSA) unit, a membrane separation unit, a cryogenic separation unit, and combinations thereof.

In an aspect, a methane conversion process for producing $C_{2+}$ hydrocarbons as disclosed herein can further comprise a step of withdrawing at least a portion of the hydrogen lean stream 52 as a purge stream 53, to yield a residual hydrogen lean stream 55. For purposes of the disclosure herein, a "purge" or "purge stream" withdrawn from the hydrogen lean stream 52 is defined as any portion of the hydrogen lean stream 52 not being returned to the reaction unit 100. As will be appreciated by one of skill in the art, and with the help of this disclosure, since the natural gas stream 30 introduced to the process comprises an inert compound, if the inert compound is not purged, it will accumulate in the $C_{2+}$ hydrocarbons production system 1000, which would interfere with the functioning of the reaction unit 100.

In an aspect, the residual hydrogen lean stream 55 (e.g., any remaining portion of the hydrogen lean stream 52) can be recycled to the reaction unit 100, for example via the methane recycle stream 10. In some aspects, the residual hydrogen lean stream 55 can be combined with any remaining portion of the inert rich stream 45 and/or the residual inert rich stream 47 to yield an inert compound recycle stream 49. The inert compound recycle stream 49 can be recycled to the reaction unit 100, for example via the methane recycle stream 10. In some aspects, the inert compound recycle stream 49 can be combined with the methane rich stream 42 to yield the methane recycle stream 10, wherein the methane recycle stream 10 is recycled to the reaction unit 100.

In an aspect, a methane conversion process for producing $C_{2+}$ hydrocarbons as disclosed herein can comprise a step of recovering $C_{2+}$ olefins 64 and/or $C_{2+}$ alkanes 62 from the at least one liquid stream 41 (e.g., $C_{2+}$ hydrocarbons liquid stream 41) in the downstream separation unit 600. The downstream separation unit 600 can comprise separation columns, such as cryogenic distillation columns (e.g., a deethanizer column, a $C_2$ splitter column, a depropanizer column, a $C_3$ splitter column, etc.).

In an aspect, the $C_{2+}$ hydrocarbons liquid stream 41 can be introduced to a deethanizer column to yield a $C_2$ hydrocarbons stream (e.g., overhead stream) and a $C_{3+}$ hydrocarbons stream (e.g., a bottoms stream). The deethanizer column can be a cryogenic distillation column. The $C_2$ hydrocarbons stream can comprise ethylene ($C_2H_4$), ethane ($C_2H_6$), and acetylene ($C_2H_2$); and the $C_{3+}$ hydrocarbons stream can comprise $C_3$ hydrocarbons and $C_4$ hydrocarbons.

In some aspects, at least a portion of the $C_2H_2$ in the $C_2$ hydrocarbons stream can be contacted with $H_2$ (e.g., hydrogen rich stream 56) to yield ethylene. Acetylene can be selectively hydrogenated to ethylene by using any suitable methodology, for example by gas phase hydrogenation.

In an aspect, an ethylene stream and an ethane stream (e.g., ethane recycle stream 12) can be recovered from at least a portion of the $C_2$ hydrocarbons stream by cryogenic distillation, for example in a $C_2$ splitter column. The ethane recycle stream 12 can be recycled to the reaction unit 100.

In an aspect, a $C_3$ hydrocarbons stream and a $C_{4+}$ hydrocarbons stream can be recovered from at least a portion of the $C_{3+}$ hydrocarbons stream, wherein the $C_3$ hydrocarbons stream comprise propylene ($C_3H_6$), and propane ($C_3H_8$). In an aspect, the $C_{3+}$ hydrocarbons stream can be conveyed from the deethanizer column to a depropanizer column (e.g., a cryogenic distillation column) for the separation and recovery of $C_3$ hydrocarbons.

In an aspect, a process for producing olefins can comprise (a) introducing a reactant mixture to an OCM reaction unit to produce a reactor effluent stream; wherein the reactant mixture comprises methane, oxygen ($O_2$), and nitrogen; wherein the methane is present in the reactant mixture in a concentration of equal to or greater than about 40 mol %; wherein the reactor effluent stream comprises $C_{2+}$ olefins, methane, $H_2$, the inert compound, water, and carbon dioxide; and wherein the mole fraction of methane in the reactant mixture is greater than the mole fraction of methane in the reactor effluent stream; (b) removing at least a portion of the water and at least a portion of the carbon dioxide from the reactor effluent stream to produce a demethanizer feed stream; (c) feeding at least a portion of the demethanizer feed stream to a demethanizer unit to produce two or more vapor streams, and at least one liquid stream; wherein the two or more vapor streams comprise a methane rich stream and an inert rich stream; wherein the mole fraction of methane in the methane rich stream is greater than the mole fraction of methane in the inert rich stream; wherein the mole fraction of inert compound in the inert rich stream is greater than the mole fraction of inert compound in the methane rich stream; and wherein the at least one liquid stream comprises $C_{2+}$ olefins; (d) heat exchanging the inert rich stream and the methane rich stream with warmer streams within the demethanizer unit; (e) withdrawing at least a portion of the inert rich stream as a purge stream; (f) recycling any remaining portion of the inert rich stream to the OCM reaction unit; (g) recycling the methane rich stream to the OCM reaction unit; (h) recovering $C_{2+}$ olefins from the at least one liquid stream in a downstream separation unit; wherein the $C_{2+}$ olefins comprise ethylene and propylene; and (i) optionally recovering $C_{2+}$ alkanes from the at least one liquid stream in a downstream separation unit; wherein the $C_{2+}$ alkanes comprise ethane; and wherein at least a portion of the $C_{2+}$ alkanes is recycled to the OCM reaction unit. In such aspect, the process for producing olefins can further comprise (i) feeding at least a portion of the inert rich stream to a hydrogen recovery unit to produce a hydrogen rich stream and a hydrogen lean stream, wherein the mole fraction of hydrogen in the hydrogen rich stream is greater than the mole fraction of hydrogen in the hydrogen lean stream; (ii) withdrawing at least a portion of the hydrogen lean stream as a purge stream; and (iii) recycling any remaining portion of the hydrogen lean stream to the OCM reaction unit.

In an aspect, a methane conversion process for producing $C_{2+}$ hydrocarbons as disclosed herein can advantageously display improvements in one or more process characteristics when compared to an otherwise similar process that does not comprise withdrawing a purge stream from an inert rich stream and recycling any remaining portion of the inert rich stream to a reaction unit. By withdrawing a purge from a stream that has an increased content of inerts (e.g., a stream such as inert rich stream 45 and/or hydrogen lean stream 52), the amount of useful compounds that is lost to the purge can be also advantageously minimized. For example, by withdrawing a purge from a hydrogen lean stream with a high inert content (e.g., hydrogen lean stream 52), the loss of hydrogen to the purge can be advantageously reduced.

In an aspect, a methane conversion process for producing $C_{2+}$ hydrocarbons as disclosed herein can advantageously display a reduced purge rate, owing to withdrawing a purge from a stream with a high inert content, which further reduces the supplemental natural gas feed rate, thereby improving the chemical carbon efficiency of the process. The capital cost for such a process can also be advantageously lower, since the process as disclosed herein reduces the need for or size of power plant equipment to derive power from the purge stream, owing to a decreased volume of purge stream. In aspects where the purge point is positioned downstream of the hydrogen removal unit, the recompression costs to recycle the residual hydrogen lean stream (e.g., comprising hydrocarbons) to the reaction unit can also be advantageously lower. For purposes of the disclosure herein the chemical carbon efficiency is defined as the ratio of the number of moles of carbon present in $C_{2+}$ hydrocarbon product streams to the number of moles of carbon in the supplemental natural gas feed.

In an aspect, a methane conversion process for producing $C_{2+}$ hydrocarbons as disclosed herein can advantageously allow for (i) reduction of the purge flow for the case where the inert content in the reactor feed is held constant; (ii) the inert content of the reactor feed to be lower, thereby reducing capital and operating costs (e.g., compression cost) of the equipment in the recycle loop; or both (i) and (ii). Additional advantages of the methane conversion process for producing $C_{2+}$ hydrocarbons as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Illustrative methane conversion processes according to the general arrangement shown in the FIGURE were simulated using steady-state process simulation software. In comparative examples, labeled "original purge location" in the tables below, the purge stream removing the inert compounds was withdrawn from the $CH_4$ recycle stream (10) upstream of methane conversion unit 100. In examples constructed according to the method of the present disclosure, the purge location was changed to one of the inert-rich overhead streams. As will be evident from the results in the tables below, the purge rates are much lower and carbon efficiency is higher for the process according to the present disclosure, regardless of the concentration of inert compound in the fresh natural gas feed.

Example 1

The comparison below illustrates the improvement in process performance when the purge point is shifted for a make-up natural gas containing 2% nitrogen.

TABLE 1

| Input parameters | (low purge and purge point shifted) | (original purge location) |
|---|---|---|
| Fresh natural gas feed (tons/hr) | 7.8 | 8.3 |
| Feed-preheat | No | No |
| Overall $CH_4/O_2$ ratio | 7.35 | 7.35 |
| $N_2$ in feed NG (mol %) | 2 | 2 |
| $C_{2+}$ product rate (tons/hr) | 4.9 | 4.9 |
| Purge flow (kg/hr) | 1127 | 1765 |
| $N_2$ in $C_1$ recycle (mol %) | 9 | 9 |
| Chemical C efficiency (%) | 72.5 | 67 |

Example 2

As inert content in fresh natural gas feed increases the process performance improvement employing the modified process scheme is even more significant as seen in the bigger difference in carbon efficiency.

TABLE 2

| Input parameters | (low purge and purge point shifted) | (original purge location) |
|---|---|---|
| Fresh natural gas feed (tons/hr) | 8.5 | 11 |
| Feed-preheat | No | No |
| Overall $CH_4/O_2$ ratio | 7.35 | 7.35 |
| $N_2$ in feed NG (mol %) | 4 | 4 |
| $C_{2+}$ product rate (tons/hr) | 4.7 | 4.7 |
| Purge flow (kg/hr) | 2076 | 4605 |
| $N_2$ in $C_1$ recycle (mol %) | 9.6 | 9.6 |
| Chemical C efficiency (%) | 67.1 | 51.7 |

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A methane conversion process for producing $C_{2+}$ hydrocarbons comprising:
   (a) introducing a reactant mixture to a reaction unit to produce a reactor effluent stream; wherein the reactant mixture comprises methane and an inert compound; wherein the methane is present in the reactant mixture in a concentration of equal to or greater than about 20 mol %; wherein the reactor effluent stream comprises $C_{2+}$ hydrocarbons, methane, the inert compound, and water and/or carbon dioxide; and wherein the mole fraction of methane in the reactant mixture is greater than the mole fraction of methane in the reactor effluent stream;
   (b) removing at least a portion of the water and/or at least a portion of the carbon dioxide from the reactor effluent stream to produce a demethanizer feed stream;
   (c) feeding at least a portion of the demethanizer feed stream to a demethanizer unit to produce two or more vapor streams, and at least one liquid stream; wherein the two or more vapor streams comprise a methane rich stream and an inert rich stream; wherein the mole fraction of methane in the methane rich stream is greater than the mole fraction of methane in the inert rich stream; wherein the mole fraction of inert compound in the inert rich stream is greater than the mole fraction of inert compound in the methane rich stream; and wherein the at least one liquid stream comprises $C_{2+}$ hydrocarbons;
   (d) withdrawing at least a portion of the inert rich stream as a purge stream;
   (e) recycling any remaining portion of the inert rich stream to the reaction unit; and
   (f) recycling the methane rich stream to the reaction unit.

2. The methane conversion process of claim 1 further comprising (i) combining the methane rich stream with the remaining portion of the inert rich stream to produce a methane recycle stream; and (ii) recycling the methane recycle stream to the reaction unit.

3. The methane conversion process of claim 1, wherein the two or more vapor streams comprise a methane rich stream and a plurality of inert rich streams.

4. The methane conversion process of claim 3, wherein two or more inert rich streams of the plurality of inert rich streams are combined to form a combined inert rich stream.

5. The methane conversion process of claim 4 further comprising (i) withdrawing at least a portion of the combined inert rich stream as a purge stream; and (ii) recycling any remaining portion of the combined inert rich stream to the reaction unit.

6. The methane conversion process of claim 4 further comprising (1) withdrawing at least a portion of at least one inert rich stream of the two or more inert rich streams as a purge stream prior to forming the combined inert rich stream; and (2) recycling the combined inert rich stream to the reaction unit.

7. The methane conversion process of claim 1, wherein the reactor effluent stream further comprises hydrogen.

8. The methane conversion process of claim 7 further comprising (i) feeding at least a portion of the inert rich stream to a hydrogen recovery unit to produce a hydrogen rich stream and a hydrogen lean stream, wherein the mole fraction of hydrogen in the hydrogen rich stream is greater than the mole fraction of hydrogen in the hydrogen lean stream; (ii) withdrawing at least a portion of the hydrogen lean stream as a purge stream; and (iii) recycling any remaining portion of the hydrogen lean stream to the reaction unit.

9. The methane conversion process of claim 1, wherein a feed stream comprising supplemental methane is introduced to the reaction unit; the demethanizer unit; a carbon dioxide removal unit located upstream of the demethanizer unit; or combinations thereof.

10. The methane conversion process of claim 9, wherein the feed stream comprising supplemental methane comprises the inert compound in a mole fraction of equal to or greater than about 0.001.

11. The methane conversion process of claim 1 further comprising recovering $C_{2+}$ olefins and/or $C_{2+}$ alkanes from the at least one liquid stream in a downstream separation unit.

12. The methane conversion process of claim 1, wherein the temperature of the inert rich stream is increased by indirect heat exchange with at least one process stream prior to the step (d) of withdrawing at least a portion of the inert rich stream as a purge stream.

13. The methane conversion process of claim 12, wherein the at least one process stream comprises the demethanizer feed stream.

14. The methane conversion process of claim 1, wherein the methane conversion process comprises oxidative coupling of methane, a single-step methane to olefins conversion, methanation, thermal cracking, ethane pyrolysis, or combinations thereof.

15. The methane conversion process of claim 1, wherein the demethanizer unit comprises one or more flash vessels and at least one fractionation column; wherein the inert rich stream is recovered as an overhead stream from the one or more flash vessels; wherein the methane rich stream is recovered as an overhead stream from the fractionation column; and wherein the at least one liquid stream is recovered as a bottoms stream from the fractionation column.

16. The methane conversion process of claim 1, wherein the inert compound is nitrogen ($N_2$).

17. A process for producing olefins comprising:
   (a) introducing a reactant mixture to an oxidative coupling of methane (OCM) reaction unit to produce a reactor effluent stream; wherein the reactant mixture comprises methane, oxygen ($O_2$), and an inert compound; wherein the methane is present in the reactant mixture in a concentration of equal to or greater than about 40 mol %; wherein the reactor effluent stream comprises $C_{2+}$ olefins, methane, hydrogen ($H_2$), the inert compound, water, and carbon dioxide; and wherein the mole fraction of methane in the reactant mixture is greater than the mole fraction of methane in the reactor effluent stream;

(b) removing at least a portion of the water and/or at least a portion of the carbon dioxide from the reactor effluent stream to produce a demethanizer feed stream;

(c) feeding at least a portion of the demethanizer feed stream to a demethanizer unit to produce two or more vapor streams, and at least one liquid stream; wherein the two or more vapor streams comprise a methane rich stream and an inert rich stream; wherein the mole fraction of methane in the methane rich stream is greater than the mole fraction of methane in the inert rich stream; wherein the mole fraction of inert compound in the inert rich stream is greater than the mole fraction of inert compound in the methane rich stream; and wherein the at least one liquid stream comprises $C_{2+}$ olefins;

(d) withdrawing at least a portion of the inert rich stream as a purge stream;

(e) recycling any remaining portion of the inert rich stream to the OCM reaction unit; and (f) recycling the methane rich stream to the OCM reaction unit.

18. The process of claim 17 further comprising (i) feeding at least a portion of the inert rich stream to a hydrogen recovery unit to produce a hydrogen rich stream and a hydrogen lean stream, wherein the mole fraction of hydrogen in the hydrogen rich stream is greater than the mole fraction of hydrogen in the hydrogen lean stream; (ii) withdrawing at least a portion of the hydrogen lean stream as a purge stream; and (iii) recycling any remaining portion of the hydrogen lean stream to the OCM reaction unit.

19. The process of claim 17 further comprising recovering $C_{2+}$ olefins from the at least one liquid stream in a downstream separation unit; wherein the $C_{2+}$ olefins comprise ethylene and propylene.

20. The process of claim 17 further comprising recovering $C_{2+}$ alkanes from the at least one liquid stream in a downstream separation unit; wherein the $C_{2+}$ alkanes comprise ethane; and wherein at least a portion of the $C_{2+}$ alkanes is recycled to the OCM reaction unit.

* * * * *